United States Patent
Sjolin

(10) Patent No.: US 10,271,803 B2
(45) Date of Patent: Apr. 30, 2019

(54) HIGH-RESOLUTION COMPUTED TOMOGRAPHY USING EDGE-ON DETECTORS WITH TEMPORALLY OFFSET DEPTH-SEGMENTS

(71) Applicant: Prismatic Sensors AB, Stockholm (SE)

(72) Inventor: Martin Sjolin, Stockholm (SE)

(73) Assignee: PRISMATIC SENSORS AB, Stockholm (SE)

(*) Notice: Subject to any disclaimer, the term of this patent is extended or adjusted under 35 U.S.C. 154(b) by 0 days.

(21) Appl. No.: 15/505,338

(22) PCT Filed: Nov. 12, 2015

(86) PCT No.: PCT/SE2015/051202
§ 371 (c)(1),
(2) Date: Feb. 21, 2017

(87) PCT Pub. No.: WO2017/082785
PCT Pub. Date: May 18, 2017

(65) Prior Publication Data
US 2017/0269008 A1    Sep. 21, 2017

(51) Int. Cl.
*A61B 6/03* (2006.01)
*G01N 23/04* (2018.01)
(Continued)

(52) U.S. Cl.
CPC ............ *A61B 6/4241* (2013.01); *A61B 6/03* (2013.01); *A61B 6/032* (2013.01); *A61B 6/035* (2013.01);
(Continued)

(58) Field of Classification Search
CPC ....... A61B 6/032; A61B 6/037; A61B 6/4208; A61B 6/4233; A61B 6/4241; A61B 6/035; G01N 23/046
(Continued)

(56) References Cited

U.S. PATENT DOCUMENTS

| 4,937,453 A | 6/1990 | Nelson |
|---|---|---|
| 5,434,417 A | 7/1995 | Nygren |

(Continued)

FOREIGN PATENT DOCUMENTS

| WO | 0055645 A1 | 9/2000 |
|---|---|---|
| WO | 2010/093314 A1 | 8/2010 |

OTHER PUBLICATIONS

International Search Report, dated Aug. 17, 2016, from corresponding PCT application.

*Primary Examiner* — Allen C. Ho
(74) *Attorney, Agent, or Firm* — Young & Thompson

(57) ABSTRACT

Disclosed is a measurement method performed by a Computed Tomography, CT, system. The CT system includes an x-ray source (60) and an x-ray detector (50) array of photon counting edge-on detectors (5), wherein each photon counting edge-on detector has a number of depth-segments, also referred to as detector elements, arranged at different spatial locations in the direction of incoming x-rays (45). The method includes to apply a time offset measurement scheme that provides a time offset between measurement periods for at least two different detector elements located at different depths, wherein the time offset is chosen so that at least two measurement periods at least partially overlaps in time. Disclosed is also a corresponding CT system (10), a control unit for a CT system and a measurement circuit for a CT system. A computer program (225) controlling a CT system is also disclosed. The disclosed technology provides for a higher sampling frequency in the angular direction (55).

29 Claims, 11 Drawing Sheets

(51) Int. Cl.
*A61B 6/00* (2006.01)
*G01N 23/046* (2018.01)
*G01T 1/29* (2006.01)

(52) U.S. Cl.
CPC ............ *A61B 6/037* (2013.01); *A61B 6/4208* (2013.01); *A61B 6/4233* (2013.01); *A61B 6/54* (2013.01); *G01N 23/046* (2013.01); *G01T 1/2985* (2013.01)

(58) Field of Classification Search
USPC .............................. 378/19, 98.8; 250/370.09
See application file for complete search history.

(56) References Cited

U.S. PATENT DOCUMENTS

| | | | | |
|---|---|---|---|---|
| 6,484,051 | B1* | 11/2002 | Daniel | G01N 23/20 |
| | | | | 250/363.03 |
| 6,546,075 | B1 | 4/2003 | Chartier et al. | |
| 6,920,196 | B2* | 7/2005 | Ueno | A61B 6/032 |
| | | | | 250/363.03 |
| 6,965,661 | B2* | 11/2005 | Kojima | G01T 1/1648 |
| | | | | 378/10 |
| 7,026,622 | B2 | 4/2006 | Kojima | G01N 23/046 |
| | | | | 250/363.02 |
| 7,053,376 | B2* | 5/2006 | Amemiya | A61B 6/032 |
| | | | | 250/363.04 |
| 7,154,989 | B2* | 12/2006 | Ueno | A61B 6/032 |
| | | | | 378/19 |
| 7,217,931 | B2* | 5/2007 | Ueno | G01T 1/2928 |
| | | | | 250/370.09 |
| 7,251,523 | B2* | 7/2007 | Kojima | A61B 6/032 |
| | | | | 250/363.03 |
| 7,291,841 | B2* | 11/2007 | Nelson | G01T 1/243 |
| | | | | 250/370.01 |
| 7,297,955 | B2* | 11/2007 | Amemiya | G01T 1/2928 |
| | | | | 250/363.04 |
| 7,297,958 | B2* | 11/2007 | Kojima | A61B 6/4241 |
| | | | | 250/363.03 |
| 7,342,234 | B2* | 3/2008 | Yanagita | G01T 1/249 |
| | | | | 250/370.15 |
| 7,446,319 | B2* | 11/2008 | Yanagita | G01T 1/2928 |
| | | | | 250/370.01 |
| 7,488,949 | B2* | 2/2009 | Ueno | A61B 6/037 |
| | | | | 250/370.15 |
| 7,511,277 | B2* | 3/2009 | Ueno | G01T 1/2985 |
| | | | | 250/363.04 |
| 7,532,703 | B2* | 5/2009 | Du | A61B 6/032 |
| | | | | 378/116 |
| 7,541,593 | B2* | 6/2009 | Yanagita | G01T 1/2985 |
| | | | | 250/370.08 |
| 7,573,040 | B2* | 8/2009 | Tkaczyk | G01T 1/249 |
| | | | | 250/370.09 |
| 7,606,347 | B2* | 10/2009 | Tkaczyk | A61B 6/032 |
| | | | | 378/19 |
| 7,613,274 | B2* | 11/2009 | Tkaczyk | A61B 6/032 |
| | | | | 378/19 |
| 7,634,061 | B1* | 12/2009 | Tümer | G01T 1/247 |
| | | | | 378/62 |
| 7,683,338 | B2* | 3/2010 | Ueno | A61B 6/032 |
| | | | | 250/370.09 |
| 7,688,944 | B2* | 3/2010 | Ritman | A61B 6/00 |
| | | | | 378/62 |
| 7,750,303 | B2* | 7/2010 | Ueno | G01T 1/2985 |
| | | | | 250/336.1 |
| 7,750,310 | B2* | 7/2010 | Seino | G01T 1/249 |
| | | | | 250/370.13 |
| 7,795,590 | B2* | 9/2010 | Takahashi | G01T 1/2018 |
| | | | | 250/363.02 |
| 8,017,906 | B2* | 9/2011 | Nelson | G01T 1/2018 |
| | | | | 250/252.1 |
| 8,183,535 | B2 | 5/2012 | Danielsson et al. | |
| 8,299,440 | B2* | 10/2012 | Wainer | G01T 1/17 |
| | | | | 250/363.04 |
| 8,483,352 | B2* | 7/2013 | Hoffman | A61B 6/032 |
| | | | | 378/19 |
| 8,483,353 | B2* | 7/2013 | Hoffman | A61B 6/032 |
| | | | | 378/19 |
| 8,488,736 | B2* | 7/2013 | Hoffman | A61B 6/032 |
| | | | | 378/19 |
| 8,513,617 | B2* | 8/2013 | Iwanczyk | G01T 1/243 |
| | | | | 250/394 |
| 8,581,200 | B2* | 11/2013 | Engel | G01T 1/2928 |
| | | | | 250/370.09 |
| 8,653,471 | B2* | 2/2014 | Proksa | A61B 6/032 |
| | | | | 250/363.01 |
| 8,735,832 | B2* | 5/2014 | Chappo | G01T 1/2018 |
| | | | | 250/363.01 |
| 8,772,726 | B2* | 7/2014 | Herrmann | A61B 6/032 |
| | | | | 250/361 R |
| 8,913,711 | B2* | 12/2014 | Moriyasu | A61B 6/03 |
| | | | | 378/4 |
| 8,923,588 | B2* | 12/2014 | Laurence | G01T 1/2985 |
| | | | | 382/131 |
| 8,941,076 | B2* | 1/2015 | Abraham | G01T 1/171 |
| | | | | 250/336.1 |
| 8,975,587 | B2* | 3/2015 | Yamada | G01T 1/1647 |
| | | | | 250/363.03 |
| 9,029,789 | B2* | 5/2015 | Shibuya | G01T 1/2985 |
| | | | | 250/367 |
| 9,164,183 | B2* | 10/2015 | Kraft | G01T 1/40 |
| 9,268,035 | B2* | 2/2016 | Herrmann | G01T 1/17 |
| 9,301,378 | B2 | 3/2016 | Steadman Booker | G01T 1/24 |
| 9,304,211 | B2* | 4/2016 | Goertzen | G01T 1/2018 |
| 9,347,893 | B2* | 5/2016 | Nelson | G01N 23/04 |
| 9,351,701 | B2* | 5/2016 | Yamakawa | A61B 6/025 |
| 9,354,331 | B2* | 5/2016 | Sagoh | A61B 6/032 |
| 9,417,339 | B2* | 8/2016 | Spahn | G01T 1/247 |
| 9,488,739 | B2* | 11/2016 | Pelc | G01T 1/247 |
| 9,517,045 | B2* | 12/2016 | Kang | G01N 23/087 |
| 9,804,274 | B2* | 10/2017 | Moskal | G01T 1/1603 |
| 9,993,220 | B2* | 6/2018 | Danielsson | A61B 6/4233 |
| 2004/0251419 | A1 | 12/2004 | Nelson et al. | |
| 2010/0204942 | A1 | 8/2010 | Danielsson et al. | |
| 2010/0270462 | A1 | 10/2010 | Nelson et al. | |
| 2011/0291020 | A1 | 12/2011 | Iwanczyk et al. | |

* cited by examiner

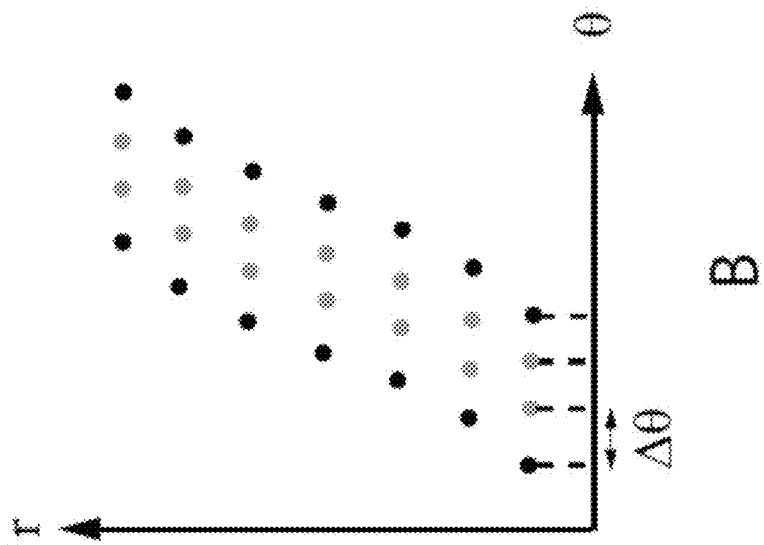
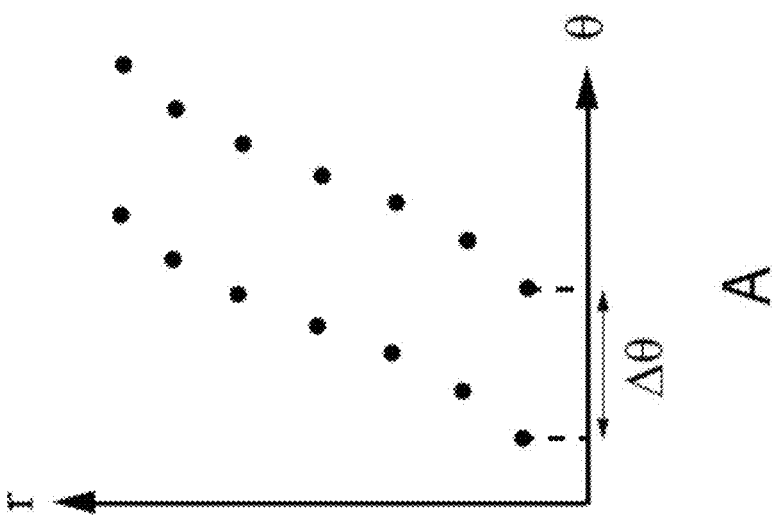
Fig. 8

HIGH-RESOLUTION COMPUTED TOMOGRAPHY USING EDGE-ON DETECTORS WITH TEMPORALLY OFFSET DEPTH-SEGMENTS

TECHNICAL FIELD

The proposed technology relates to a measurement method performed by a Computed Tomography system. The proposed technology also relates to devices and systems configured to perform the measurement method.

BACKGROUND

Radiographic imaging such as x-ray imaging has been used for years in medical applications and for non-destructive testing.

Normally, an x-ray imaging system includes an x-ray source and an x-ray detector array consisting of multiple detectors comprising one or many detector elements (independent means of measuring x-ray intensity/fluence). The x-ray source emits x-rays, which pass through a subject or object to be imaged and are then registered by the detector array. Since some materials absorb a larger fraction of the x-rays than others, an image is formed of the subject or object.

An example of a commonly used x-ray imaging system is an x-ray computed tomography, CT, system, which may include an x-ray tube that produces a fan- or cone beam of x-rays and an opposing array of x-ray detectors measuring the fraction of x-rays that are transmitted through a patient or object. The x-ray tube and detector array are mounted in a gantry that rotates around the imaged object. An illustration of a fan beam CT geometry is shown in FIG. 3.

The dimensions and segmentation of the detector array affect the imaging capabilities of the CT system. A plurality of detector elements in the direction of the rotational axis of the gantry, i.e. the z-direction of FIG. 3 enables multi-slice image acquisition. A plurality of detector elements in the angular direction ($\xi$ in FIG. 3) enables measurement of multiple projections in the same plane simultaneously and this is applied in fan/cone-beam CT. Most conventional detectors are so called flat-panel detectors, meaning that they have detector elements in the slice (z) and angular ($\xi$) directions.

X-ray detectors made from low-Z materials need to have a substantial thickness in the direction of the x-ray beam in order to have sufficient detection efficiency to be used in CT. This can be solved by, for example, using an "edge-on" geometry, as in U.S. Pat. No. 8,183,535, in which the detector array 50 is built up of a multitude of edge on detectors 5, which comprise thin wafers of a low-atomic number material, oriented with the edge towards the impinging x-rays 45. FIG. 2 shows a schematic illustration of an array of edge-on detectors 5, showing the position of the x-ray source 60, the direction of the x-rays 45, the detector array 50, a single edge-on detector 5 and the angular direction 55 of movement of the detector array 50. It is common that each photon-counting edge-on detector 5 has a plurality of detector elements 15 on a 2D grid on the wafer. An example of an edge-on semiconductor wafer is illustrated in FIG. 1, which shows the different detector elements 15 in a column on the detector array 50 and the direction of the impinging x-rays 45. Each individual wafer is, for example, oriented such that it has detector elements 15 in the slice direction (z) and in the direction of the x-rays 45, as schematically illustrated in FIG. 3. The edge-on geometry for semiconductor detectors is also suggested in U.S. Pat. Nos. 4,937,453, 5,434,417, US 2004/0251419 and WO 2010/093314. Wafer detectors that are oriented with a slight angle with respect to the direction of the x-rays 45 are normally also included in the term "edge-on".

Detector elements 15 at different depths into the detector material with respect to the impinging x-rays 45 will be referred to as different "depth segments". The detector elements 15 at different depths are generally aligned such that several detector elements 15 (from different depths) measure the same X-rays 45.

FIG. 9 is a schematic diagram illustrating a semiconductor detector module implemented as a multi chip module similar to an exemplary embodiment U.S. Pat. No. 8,183,535. In this example, the detector elements 15 are organized in three depth segments with respect to the direction of the incoming x-rays 45. This example shows how the semiconductor detector module also can have the function of substrate in a Multi Chip Module (MCM). The signal is routed 37 from the detector elements 15 to inputs of parallel processing circuits (e.g. ASICs) 30. It should be understood that the term Application Specific Integrated Circuit (ASIC) is to be interpreted broadly as any general circuit used and configured for a specific application. The ASIC processes the electric charge generated from each x-ray and converts it to digital data, which can be used to obtain measurement data such as a photon count and/or estimated energy. The ASICs are configured for connection to digital data processing circuitry 20 so the digital data may be sent to further digital data processing circuitry 20 and/or memories located outside of the MCM and finally the data will be the input for image processing to generate the reconstructed image.

For a given rotational position, each detector element 15 measures the transmitted x-rays 45 for a certain projection line. Such a measurement is called a projection measurement. The collection of projection measurements for many projection lines is called a sinogram. The sinogram data is utilized through image reconstruction to obtain an image of the interior of the imaged object. Each projection line (a point in the sinogram) is given by an angular coordinate, $\theta$, and a radial coordinate, r, as defined in FIG. 7. Each measurement with a detector element 15 at a specific coordinate given by (r,$\theta$) is a sample of the sinogram. More samples in the sinogram generally lead to a better representation of the real sinogram and therefore also a more accurately reconstructed image. An example of how a detector array 50, similar to that displayed in FIG. 3, samples the sinogram space is shown in FIG. 8 A for two angular positions of the gantry separated by $\Delta\theta$. The different r positions of the samples come from the different detector elements 15 in the detector array 50.

Generally, the gantry rotates continuously and each detector element 15 measures the x-rays 45 within a frame time. A measurement period is here defined as the interval in time during which a certain detector element 15 is occupied with a measurement. The length of the measurement period can be, but does not have to be, equal to the frame time. The measurement period is much smaller than the total data acquisition time and multiple measurement periods follow directly after each other throughout the measurement. The length of the measurement period is referred to as the temporal sampling interval and the reciprocal of the sampling interval 1/T is referred to as the sampling frequency. The angular sampling interval of the CT system 10 is given by the angular velocity of the gantry, $\omega = d\theta/dt$, and the temporal sampling interval, T, by $\Delta\theta = \omega T$. A schematic illustration of the angular sampling is displayed in FIG. 4, where the photon counting edge-on detector 5 and the X-ray source 60 are illustrated for two different positions separated in time by the sampling interval T. The radial coordinate for all projection lines corresponding to a specific detector element 15 is invariant to the rotation of the gantry.

In order to perform an accurate image reconstruction from tomographic data, it is essential that there are a sufficient amount of angular samples. Insufficient angular sampling can lead to artifacts in the image, aliasing and poor resolution.

One way to increase the angular sampling frequency (without using specific oversampling schemes, as described in a later) is to decrease the temporal sampling interval T. This is, however, often limited by the detector electronics. Another way to obtain higher angular sampling frequency is to decrease the rotation speed ω and lower the flux (in order not to increase the patient dose). This comes with a noise penalty for conventional energy integrating detectors since less flux implies more relative electronic noise when integrating the signal. For photon counting detectors, however, decreasing the flux does not come with a noise penalty, since there is no integration process. Therefore, it is possible to use a higher sampling rate in photon-counting CT compared to conventional CT.

There are several oversampling schemes developed for computed tomography, for example: "quarter-detector offset" and "flying focal spot". The "quarter-detector offset" method is well known and implies that the detector elements are spatially offset with respect to the central line of the fan-beam by one quarter of the detector width. This implies that the projections at θ and θ+180 degrees are not the same, but offset by half a pixel. This produces an oversampling (two times higher) in the radial direction. The method "flying focal spot" implies that the focal spot is moved during the measurement in order to produce more projection lines. This method can produce an oversampling in both the radial and the angular directions. For edge-on detectors, the flying focal-spot method has the disadvantage that the spectral response of the detector changes if you change the alignment of the detector with respect to the source by moving the source.

In U.S. Pat. No. 7,696,481 there is described a method for oversampling using for multi-layer detectors where the detector elements in the different layers are spatially offset with resect to each other. This produces an oversampling in both the radial and the angular direction. However, when low-Z materials are used as detector material, the fraction of photons which scatter in the detector is significant, therefore it can be beneficial to have anti-scatter modules interfolded between at least a subset of the detector modules, as described in U.S. Pat. No. 8,183,535 B2. If such anti-scatter modules are used, it is preferable to align the anti-scatter modules (and the detectors modules) with the direction of the x-rays 45 in order to maintain detection efficiency (if not aligned, the anti-scatter modules will also absorb primary radiation which otherwise could be collected by the detector). Therefore, if anti-scatter modules that are interfolded between the detector modules are used, an oversampling scheme that includes spatial shift between the detector elements in the different depth segments is impractical.

SUMMARY

It is a general object of the proposed technology to provide a mechanism whereby a Computed Tomography, CT, technology can be provided with a higher sampling frequency in the angular direction.

It is a more specific object to provide a Computed Tomography, CT, system that provides for higher sampling frequency in the angular direction.

Another object is to provide a measurement method that leads to a higher sampling frequency in the angular direction.

Still another object is to provide a control unit for a Computed Tomography, CT, system that provides for a higher sampling frequency in the angular direction.

Yet another object is to provide a measurement circuit in a Computed Tomography, CT, system that provides for a higher sampling frequency in the angular direction.

A further object is to provide a computer program to control a CT system that provides for higher sampling frequency in the angular direction.

According to a first aspect there is provided a Computed Tomography, CT, system comprising an x-ray source and an x-ray detector array of photon counting edge-on detectors, wherein each edge-on detector has a number of depth-segments, also referred to as detector elements, arranged at different spatial locations in the direction of incoming x-rays, wherein the CT system is configured to operate based on a time offset measurement scheme for providing a time offset between measurement periods for at least two different detector elements located at different depths, wherein the time offset is chosen so that the respective measurement periods of the at least two different detector elements at least partially overlaps in time.

According to a second aspect there is provided a measurement method performed by a CT system, the CT system comprising an x-ray source and an x-ray detector array of photon counting edge-on detectors, wherein each edge-on detector has a number of depth-segments, also referred to as detector elements, arranged at different spatial locations in the direction of incoming x-rays, wherein the method comprises to apply a time offset measurement scheme that provides a time offset between measurement periods for at least two different detector elements located at different depths, wherein the time offset is chosen so that the respective measurement periods of the at least two different detector elements at least partially overlaps in time.

According to a third aspect there is provided a control unit for a Computed Tomography, CT, system that comprises an x-ray source and an x-ray detector array of photon counting edge-on detectors, wherein each edge-on detector has a number of depth-segments, also referred to as detector elements, arranged at different spatial locations in the direction of incoming x-rays, wherein the control unit is configured to control the CT system to operate based on a time offset measurement scheme for providing a time offset between measurement periods for at least two different detector elements located at different depths, wherein the time offset is chosen so that the respective measurement periods of the at least two different detector elements at least partially overlaps in time.

According to a fourth aspect there is provided a measurement circuit in a Computed Tomography, CT, system comprising an x-ray source and an x-ray detector array of photon counting edge-on detectors, wherein each edge-on detector has a number of depth-segments, also referred to as detector elements, arranged at different spatial locations in the direction of incoming x-rays, wherein the measurement circuit is configured to operate based on a time offset measurement scheme for providing a time offset between measurement periods for at least two different detector elements located at different depths, wherein the time offset is chosen so that the respective measurement periods of the at least two different detector elements at least partially overlaps in time.

According to a fifth aspect there is provided a computer program comprising instructions, which when executed by at least one processor cause the processor(s) to control a CT system comprising an x-ray source and an x-ray detector array of photon counting edge-on detectors, wherein each edge-on detector has a number of depth-segments, also referred to as detector elements, arranged at different spatial locations in the direction of incoming x-rays, so that the CT system operate based on a time offset measurement scheme for providing a time offset between measurement periods for at least two different detector elements located at different depths, wherein the time offset is chosen so that at least two measurement periods at least partially overlaps in time.

Insufficient angular sampling frequency leads to sampling artifacts, aliasing and impaired spatial resolution in the reconstructed CT image. The described method is an effective way to increase the angular sampling frequency for edge-on detectors by utilizing the built-in redundancy of the depth segments on the detector. Higher sampling frequency allows higher gantry rotation speeds without introducing artifacts. Also, if the method is used to oversample the signal, then it will not be necessary to low-pass filter the data during the image reconstruction to prevent aliasing, thus saving more of the original image data. The proposed method is easily implemented in today's edge-on detectors.

BRIEF DESCRIPTION OF THE DRAWINGS

FIG. 8 is a schematic diagram illustrating the sampling of the sinogram.

DETAILED DESCRIPTION

Figure 1:
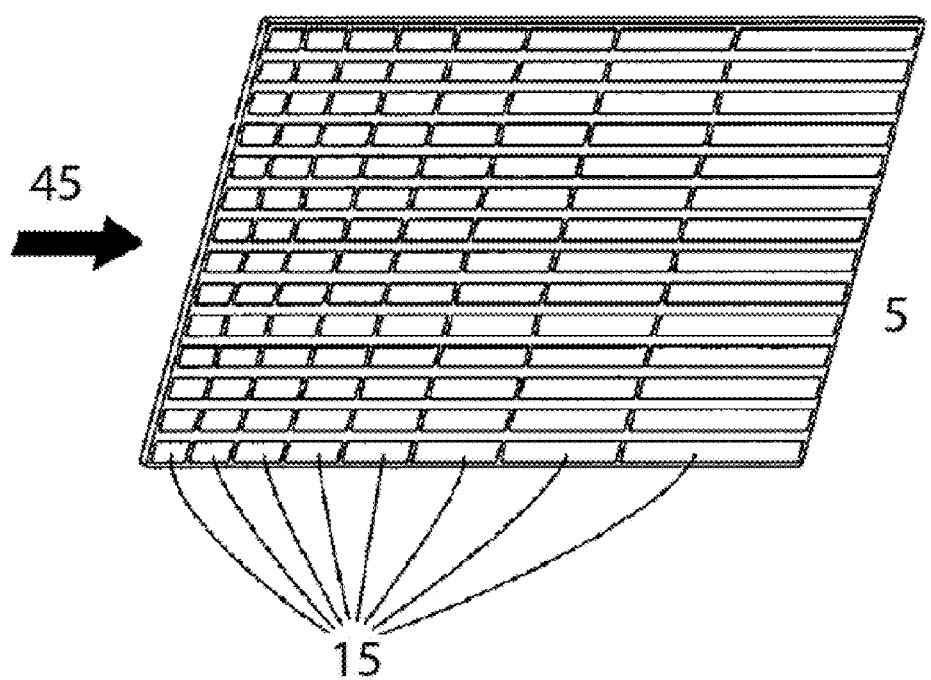
FIG. 1 is a schematic diagram illustrating an example of a single edge-on photon counting detector.

Throughout the drawings, the same reference designations are used for similar or corresponding elements.

For a better understanding of the proposed technology, it may be useful to begin with a brief system overview and/or analysis of the technical problem.

According to the proposed technology, a temporal offset is introduced between the start measurement periods of the detector elements in the different depth segments on an edge-on detector. Since the gantry rotates continuously, an offset in time corresponds to an offset in the angular coordinate of the measurements from the different depth segments, thus producing a higher sampling frequency in the angular direction. The sampling frequency can in practice be increased by the number of depth segments on the detector. Also, if the gantry rotates in helical mode, i.e. a detector element performs the measurements on a spiral with respect to the imaged object, then this method also achieves higher sampling rate in the axial (z) direction.

Increasing the angular sampling frequency has the potential to reduce aliasing, improve the spatial resolution and suppress sampling artifacts. The method can also be used to allow faster image acquisition since the gantry can be rotated faster while maintaining the angular sampling rate.

The proposed technology aims to provide mechanisms whereby a higher angular sampling frequency can be obtained from measurements performed by a Computed Tomography system, CT system. To this end there is proposed a measurement method and corresponding devices aimed at providing such a mechanism.

The proposed technology therefore provides a measurement method performed by a Computed Tomography system, CT system 10. The CT system 10 comprising an x-ray source 60 and an x-ray detector array 50 of photon counting edge-on detectors 5, wherein each photon counting edge-on detector 5 has a number of depth-segments, also referred to as detector elements 15, arranged at different spatial locations in the direction of incoming x-rays 45. The method comprises to apply a time offset measurement scheme that provides a time offset between measurement periods for at least two different detector elements 15 located at different depths, wherein the time offset is chosen so that at least two measurement periods at least partially overlap in time.

Figure 5:
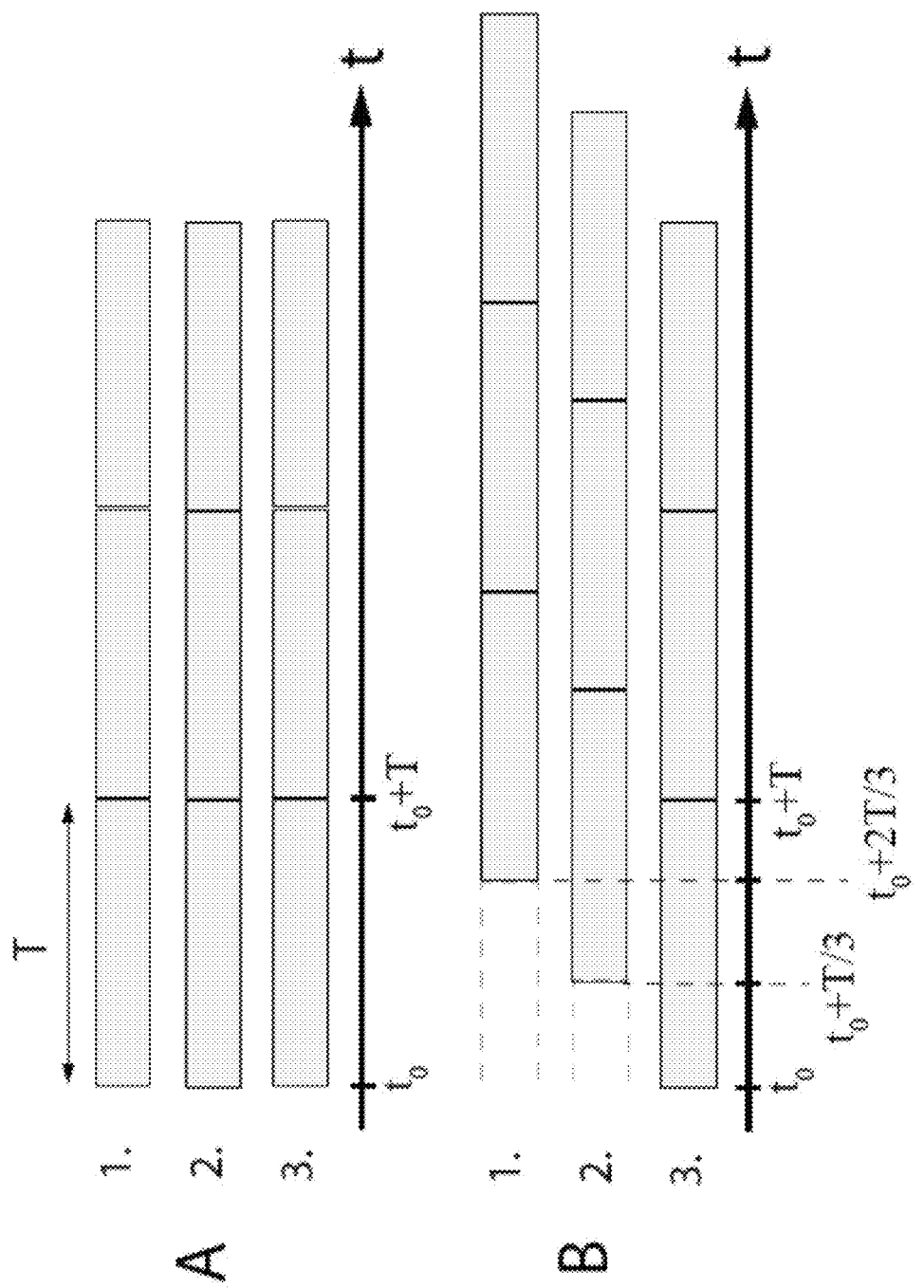
FIG. 5 is a schematic diagram illustrating two different time-sampling schemes for a detector with three depth segments, with and without an offset between the measurement periods.

Put in slightly different words, there is provided a measurement method performed by a CT system 10. According to the method, a time offset measurement scheme is applied to enable a higher angular sampling frequency which in turn leads to a richer measurement output per measurement time. The applied time offset measurement scheme controls the time settings when measurements of various detector elements 15 in the X-ray detector array 50 of photon counting edge-on detectors 5 are initiated. According to the method, the measurements performed by at least two detector elements 15 located at different depths are initiated with a relative time delay. FIG. 5 provides an illustration of a simplified case of an X-ray detector array 50 of photon counting edge-on detectors 5 having three different detector elements located at different depths. According to an example embodiment of the proposed method the time offset scheme acts to initiate the first detector element to perform a measurement at $t_0$, the applied time offset scheme then initiates the second detector element to perform a measurement at the time $t_0+T/3$, where T denotes the sampling period or integration period for the detectors. In this illustrative example a third detector element located at different depth from both the first and second detector element is then initiated to perform a measurement at $t_0+2T/3$. As can be seen in FIG. 5, at least two of the measurement periods of the detector elements overlap during the measurement procedure. This ensures that a higher angular sampling frequency is obtained. The example provided by the embodiment of FIG. 5 is merely an illustrative example. Other measurement schemes are possible, it is, for example, possible to form groups of depth segments for which the same offset is applied. Within each group of depth segments, the detector elements initiate the measurements at the same time. With this offset scheme, the sampling frequency is lower than if we were to have a unique time offset for each depth segment, but there is still oversampling, if there are at least two different groups of depth segments with a time offset with respect to each other. However, for each projection line, more statistics is acquired if the depth segments are grouped, which can be beneficial when using some kinds of image reconstruction algorithms.

It should also be noted that the duration of the measurement periods for different detector elements located at different depths may vary. That is, a first detector element may be controlled to perform measurements during a specifically set measurement period that is different from the measurement period of a second detector element controlled to perform measurements during a measurement period time offset from the measurement period of the first detector. It is possible to accord different measurement periods for all, or a subset, of different detector elements within an edge-on detector.

According to a particular embodiment there is provided a method, wherein the at least two different detector elements comprises three or more different detector elements and wherein the time offset is chosen so that at least two measurement periods of the three or more different detector elements at least partially overlap in time.

According to another particular embodiment of the proposed technology there is provided a method, wherein the size of the time offset is further chosen to be a fraction of the time duration of at least one of the measurement period(s).

In other words the size or duration of the time offset between two measurement initiations are chosen so that a desirable angular sampling pattern is achieved. By selecting the offset to be a fraction of one of the measurement periods, one ensures that an increase in the angular sampling frequency is achieved.

A possible embodiment provides a method that comprises to apply a time offset measurement scheme that provides a time offset between the measurement periods for different detector elements of the same edge-on detector.

In other words, there is provided a measurement, or sampling, scheme for detector elements that are arranged on a single detector wafer, thus limited by the necessary relative geometry of the detector elements. By introducing a time offset between the measurement periods of the different detector elements, the sampling patterns can be distributed in the angular direction such that a higher sampling rate is achieved.

By way of example, the proposed technology provides an embodiment of a method, wherein the method comprises to apply the time offset to a number of adjacent edge-on detectors.

According to this embodiment a common time offset may be provided to a number of adjacent edge-on detectors. A common time offset scheme will simplify the data processing steps, since the same data processing steps can be applied to the data from each detector without extra consideration about unique sampling patterns. Also, a common time offset scheme ensures that the object is uniformly sampled in the angular direction, which may prevent non-uniformities in the image such as streaks.

An optional embodiment of the proposed method provides for a measurement method wherein the measurement periods for the at least two different detector elements located at different depths are different and wherein the time offset is a fraction of the time duration of the shorter measurement period.

According to a particular embodiment of the proposed method each of the measurement periods have the same time duration.

This particular embodiment ensures that the time offset between the initiations of the measurements in the different depth segments are conserved for all consecutive measurements.

Having described a measurement method that utilizes a time offset measurement scheme, in what follows there will be described various devices and systems that are configured to operate based on the time offset measurement scheme of the proposed technology. The advantages and explanations provided with reference to the proposed method are equally valid for the devices.

According to a particular embodiment of the proposed technology there is provided a Computed Tomography, CT, system 10 comprising an x-ray source and an x-ray detector array of photon counting edge-on detectors 5, wherein each edge-on detector has a number of depth-segments, also referred to as detector elements 15, arranged at different spatial locations in the direction of incoming x-rays 45. The CT system 10 is configured to operate based on a time offset measurement scheme for providing a time offset between measurement periods for at least two different detector elements 15 located at different depths, wherein the time offset is chosen so that at least two measurement periods at least partially overlap in time.

The CT system 10 according to the proposed technology is in other words configured to operate based on a measurement scheme for providing at least partially overlapping measurement periods for at least two different detector elements 15 that are located at different depth.

Figure 2:
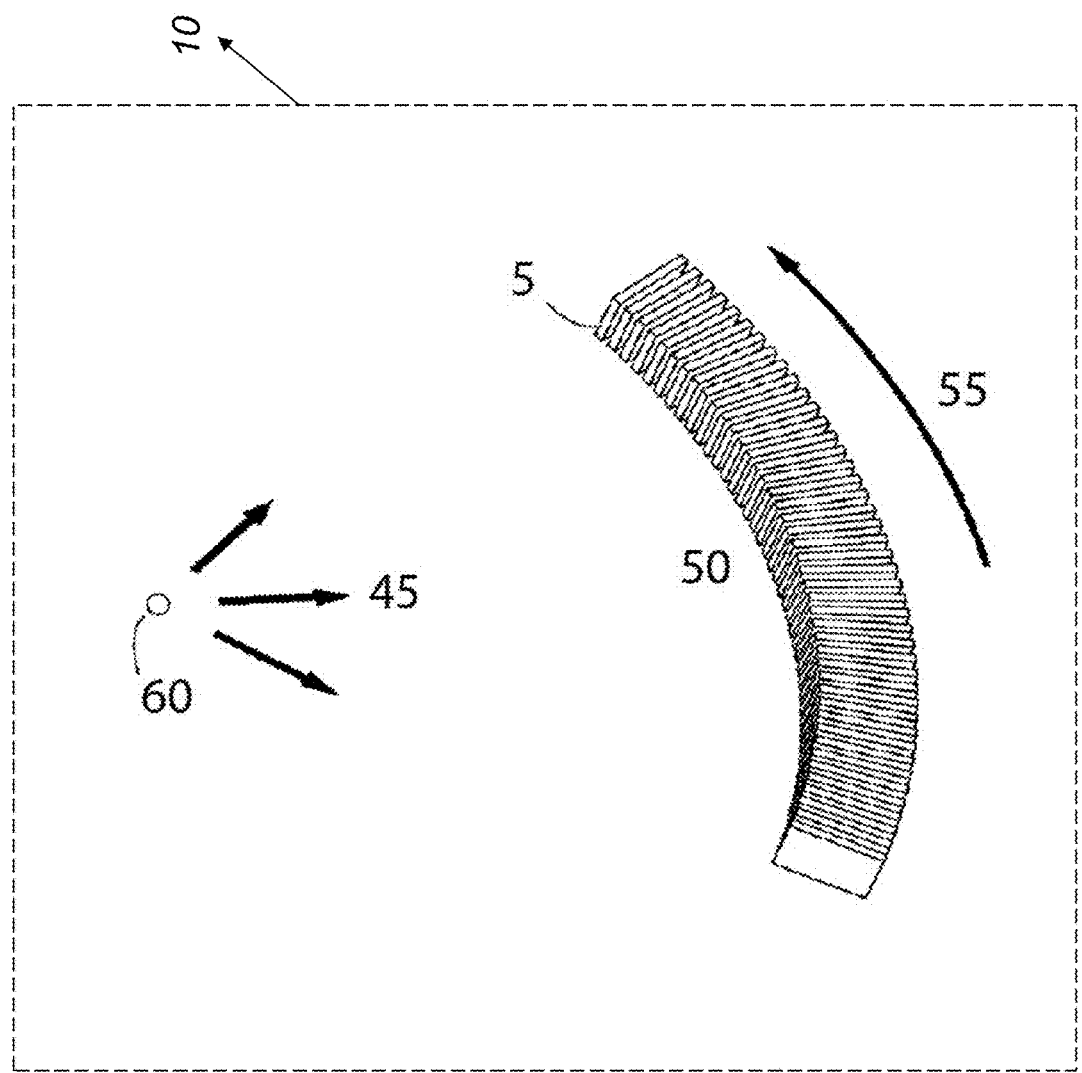
FIG. 2 is a schematic diagram illustrating an example of an array of edge-on detectors.
Figure 3:
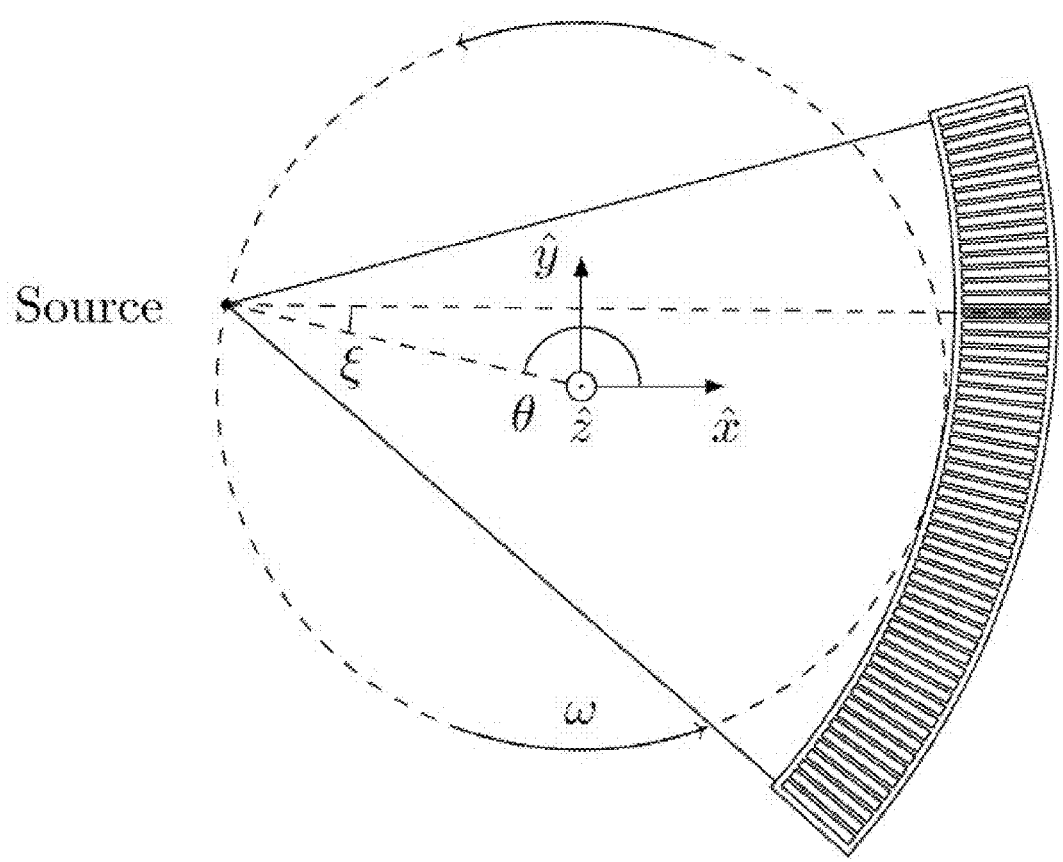
FIG. 3 is a schematic diagram illustrating an example of a fan-beam CT system.
Figure 4:
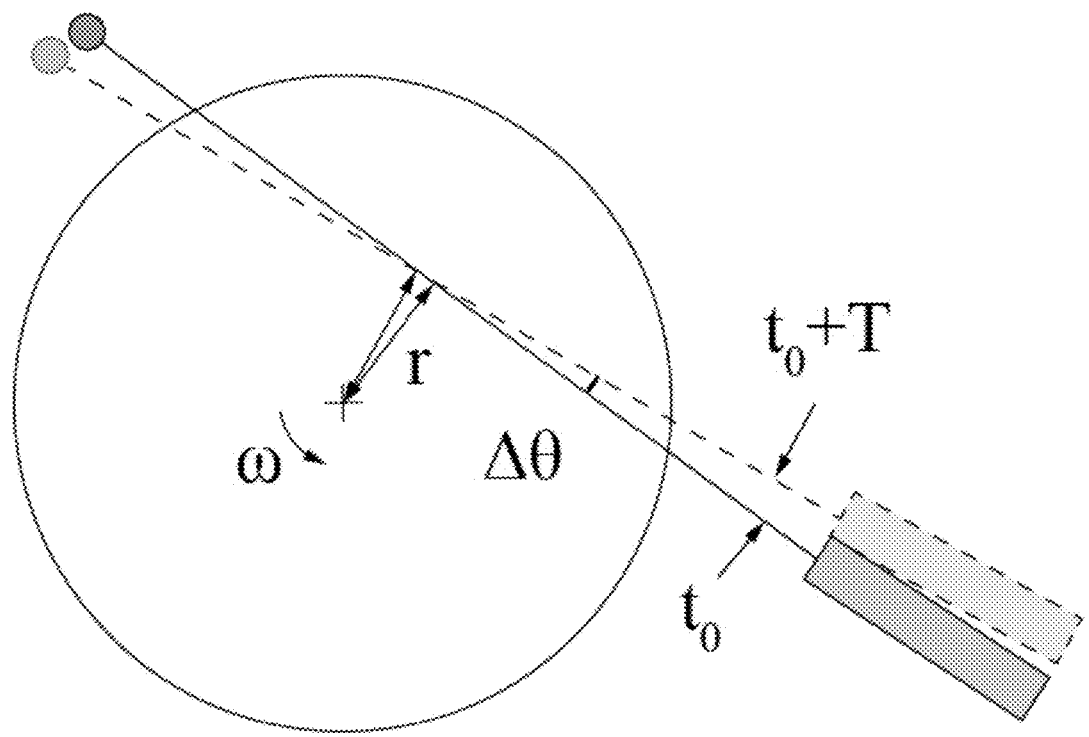
FIG. 4 is a schematic diagram illustrating the angular sampling geometry of one edge-on detector.
Figure 9:
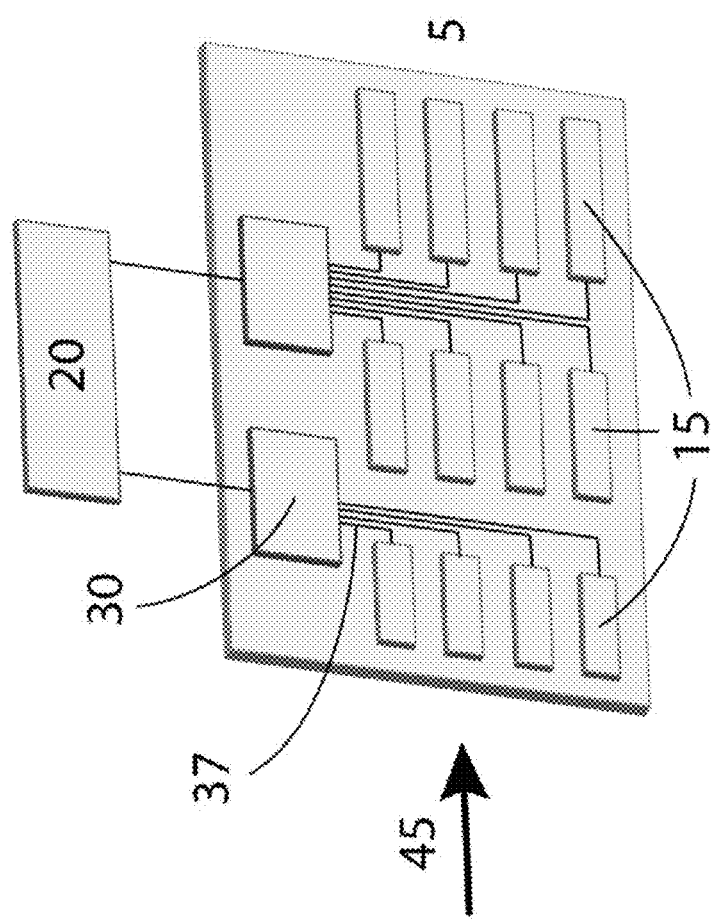
FIG. 9 is a schematic diagram illustrating an example of an edge-on detector with three depth segments, measurement circuit and a control system.

FIG. 9 shows an example of a photon counting edge-on detector 5 that may be included in a CT system 10, comprising the detector wafer, individual connections from a measurement circuit 30 to each detector element, at least two depth segments 15 in the direction of the x-rays 45. The photon counting edge-on detector 5 also comprises a measurement circuit 30 and a unit for control and read-out 20. A time offset scheme between the measurement periods of the different depth segments can be applied such that an oversampling in the angular direction is achieved during continuous rotation of the CT gantry. FIG. 2 shows an example of how the individual photon counting edge-on detectors 5 can be arranged to form x-ray detector array 50 used in a CT system 10. FIG. 2 also shows the position of the x-ray source 60, the direction of the x-rays 45.

A particular embodiment of the proposed technology provides a Computed Tomography, CT, system 10 wherein the at least two different detector elements 15 comprises three or more different detector elements 15 and wherein the time offset is chosen so that at least two measurement periods of the three or more different detector elements 15 at least partially overlap in time.

Another possible embodiment provides a CT system 10, wherein the size of the time offset is further chosen to be a fraction of the time duration of at least one of the measurement period(s).

Yet another embodiment provides a CT system 10 wherein time offset measurement scheme provides a time offset between the measurement periods for different detector elements 15 located at different depths of the same edge-on detector.

A particular embodiment provides a CT system 10 wherein a plurality of adjacent edge-on detectors are provided with the same time offset between measurement periods.

According to an optional embodiment there is provided a CT system 10 wherein the measurement periods for the at least two different detector elements 15 located at different depths are different and wherein the time offset is a fraction of the time duration of the shorter measurement period.

According to an alternative embodiment there is provided a CT system 10 wherein each of the measurement periods have the same time duration.

Below follows a number of detailed embodiments of the proposed technology. These embodiments are merely exemplary and are intended to facilitate the understanding of the proposed technology. The provided embodiments should therefore not be construed as limiting.

Figure 6:
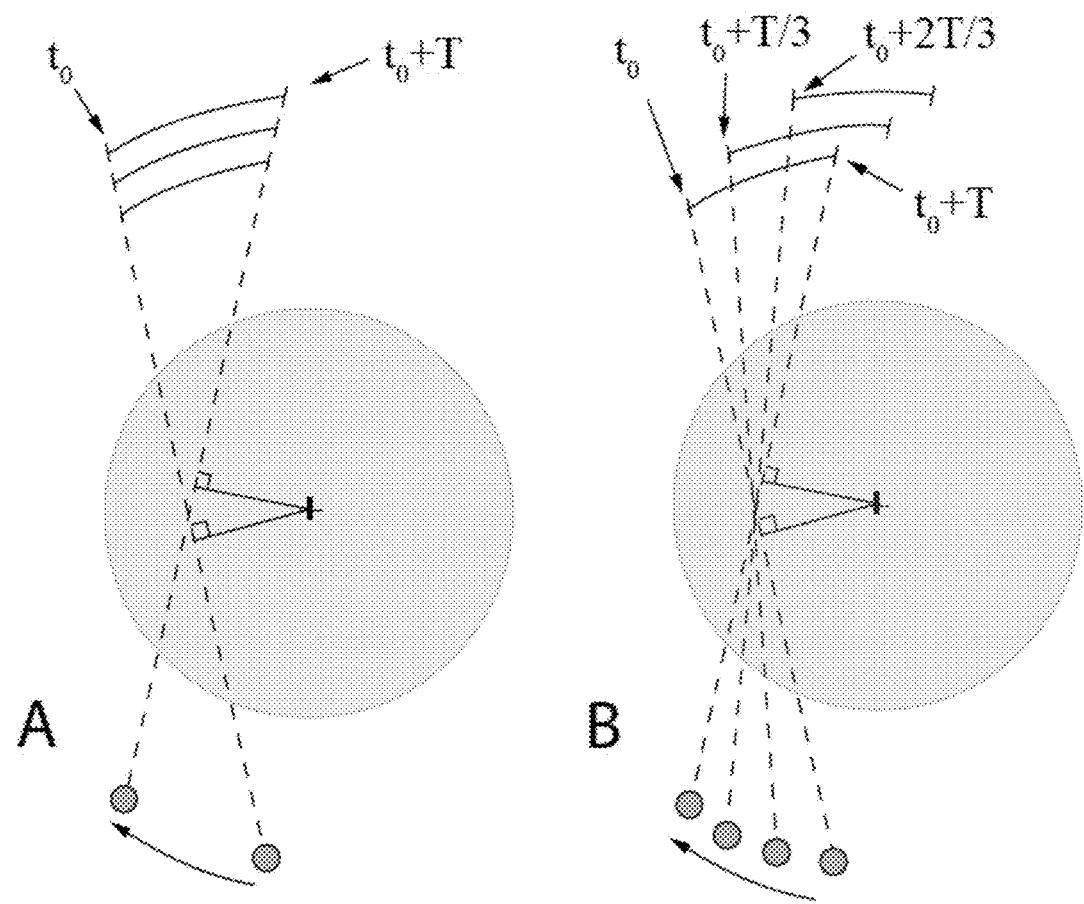
FIG. 6 is a schematic diagram illustrating the position of the detector elements in a column of three depth segments at the start and end of a measurement period.
Figure 7:
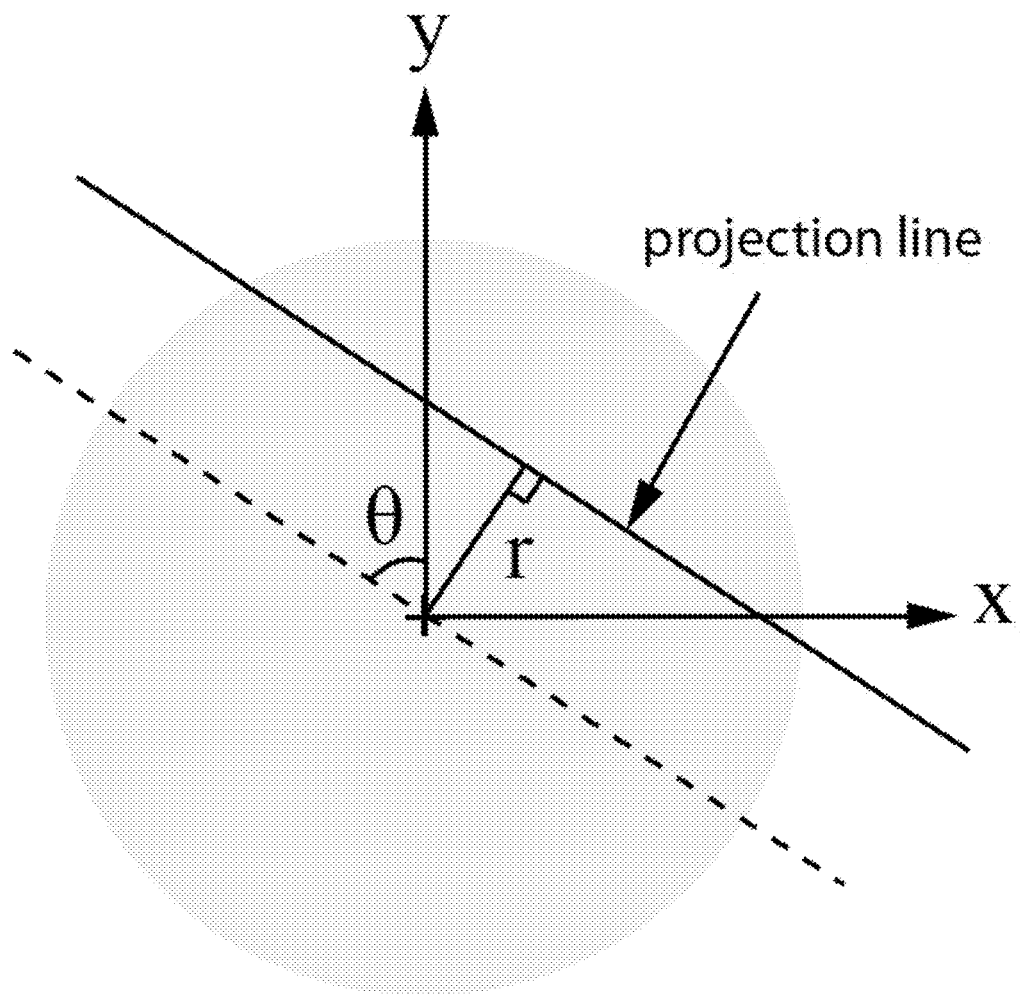
FIG. 7 is a schematic diagram illustrating the definitions of the sinogram coordinates.

In one example embodiment, the offset pattern is such that the start time of the measurement periods of the different depth segments are evenly distributed over the measurement period (T). For example, in the case of three depth segments, if the first segment starts a measurement period at $t_0$, then the second segment starts at $t_0+T/3$ and the third segment starts at $t_0+2T/3$. A new measurement for the first segment it then initiated at $t_0+T$ and so on. FIG. 5 shows a schematic illustration of the applied time offset between the measurement periods. This offset pattern implies that the projection measurements from the different depth segments are evenly distributed in the angular direction. An illustration of the angular sampling due to this offset pattern is showed in FIG. 6, where A shows the position of the detector elements at the beginning and the end of the measurements periods which starts at $t_0$ and ends at $t_0+T$ for all three depth segments. B shows the offset of the angular sampling due of an offset of the measurement periods of the different depth segments. FIG. 8 shows how the sampling scheme in the sinogram changes when applying the time offset between the measurement periods, where A shows the sampling scheme without offset and B shows the sampling scheme with offset.

If the measurement periods for the detector elements in all depth segments are synchronized in time, then all detector elements measure along the same projection line, i.e. same position $(r,\theta)$ in the sinogram.

It is common to align the detector elements on the edge-on detector with respect to the source such that a specific x-ray beam, i.e. projection line, illuminates one detector element of each depth segment. Let us call the detector elements that measure the same projection line a column. At each moment in time, all detector elements in the column measure the same projection line. The measurement period defines a time window during which the projection data is collected, and for continuous rotation, the angular coordinate of the measured projection line changes over time, which implies that a measurement consists of data from a set of projection lines with different angular coordinates defined by when the measurement periods is initiated and terminated. Now, if the measurement periods of all detector elements in a column are initiated and terminated simultaneously, i.e. the measurement periods are synchronized in time, the all the detector elements in the column collect data from the same set of projection lines for each measurement period. On the other hand, if the measurement periods are offset in time, i.e. there if a shift in time between the initiation and termination of the measurements carried out by the different detector elements in the column, then each detector element in the column collects data from a different set of projection lines.

In another example embodiment, groups of depth-segments are formed and a temporal offset between the measurement periods of the groups is applied. This can be beneficial if the number of counts in each projection measurement is very low, since low counts can lead to errors in the reconstruction algorithm and grouping the depth segments increases the statistics for each projection measurement.

In yet another example embodiment, an offset between the measurement periods of the depth-segments can be used to ensure that the measurements from depth segments of a misaligned detector are performed on the same projection line, given that the misalignment of the detector is in the direction of rotation of the gantry. In this case, the offset pattern is given by the degree of misalignment of the edge-on detectors with respect to the direction of the x-rays 45.

If the amount of data produced using this scheme is too large to be practical due to limited data read-out bandwidth, then a decimation of the data can be performed prior to the read-out. The benefit of reducing aliasing is still there since the highly sampled data can be low-pass filtered during the decimation, thus removing high frequency content, which could otherwise cause aliasing.

Having described a few illustrative examples of the proposed technology, below will follow a detailed description of a control unit for a Computed Tomography, CT, system, where the control unit is configured to control the CT system to operate based on the time offset measurement scheme of the proposed technology.

The proposed technology also provides a control unit 20 for a Computed Tomography, CT, system 10 that comprises an x-ray source and an x-ray detector array of photon counting edge-on detectors 5, wherein each edge-on detector has a number of depth-segments, also referred to as detector elements 15, arranged at different spatial locations in the direction of incoming x-rays 45. The control unit 20 is configured to control the CT system 10 to operate based on a time offset measurement scheme for providing a time offset between measurement periods for at least two different detector elements 15 located at different depths, wherein the time offset is chosen so that at least two measurement periods at least partially overlaps in time.

Figure 10:
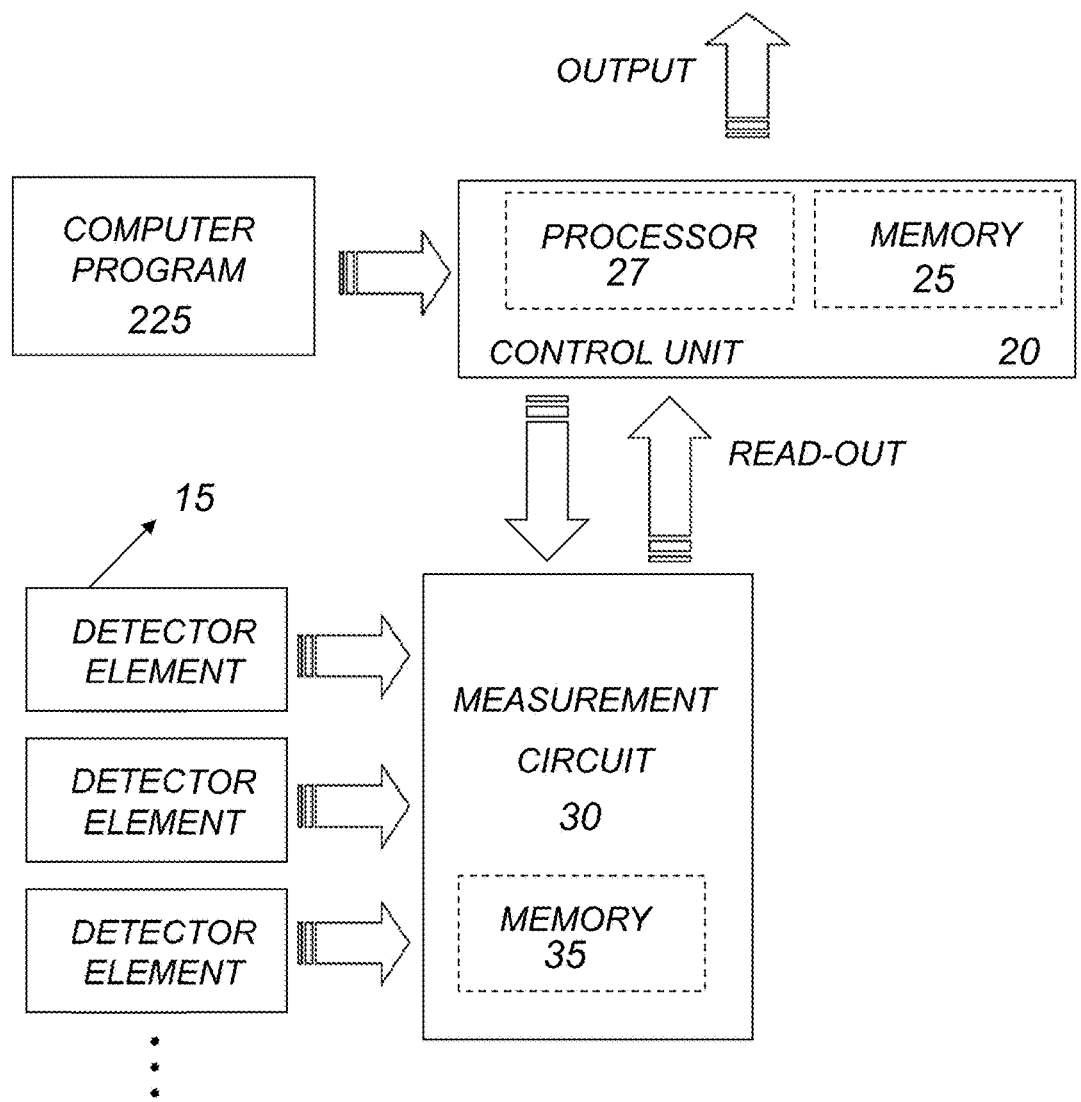
FIG. 10 is a schematic flow diagram illustrating a method for implementing a time offset measurement scheme in an edge-on detector system.

FIG. 10 displays a schematic illustration of a control unit 20 configured to control a CT system 10 comprising edge-on detectors. The control unit 20 may comprise a memory 35 and one or several processors or processing circuitries 27. Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

A computer program may in particular embodiments program the control unit 20 and/or the memory 25 that the control system may comprise. The CT system 10 may according to a particular embodiment be controlled by a computer program 225. The proposed technology therefore provides a computer program 225 comprising instructions, which when executed by at least one processor 27, cause the processor(s) to control a CT system 10 that comprises an x-ray source 60 and an x-ray detector array 50 of photon counting edge-on detectors 5, wherein each photon counting edge-on detector 5 has a number of depth-segments, also referred to as detector elements 15, arranged at different spatial locations in the direction of incoming x-rays 45, so that the CT system 10 operate based on a time offset measurement scheme for providing a time offset between measurement periods for at least two different detector elements 15 located at different depths, wherein the time offset is chosen so that at least two measurement periods at least partially overlaps in time.

The computer program 225 may in certain embodiments also comprise instructions for changing the measurement scheme used by the CT system 10.

In FIG. 10, each detector element 15 on a photon-counting edge-on detector 5 is individually connected to a measurement circuit 30. The measurement circuit 30 processes the electric charge generated from each x-ray 45 and converts it to digital data, which can be used to obtain measurement data such as a photon count. The measurement circuit 30 may comprise one or many counters, which count the number of x-rays 45 detected by a detector element 15 within a measurement period. The measurement circuit 30 may in particular embodiments comprise a memory 35. The measurement circuit 30 in turn is controlled by and communicates with the control unit 20. The control unit 20 can read out data from the measurement circuit 30. The control unit 20 may in particular embodiments comprise a memory 25. The control unit 20 is configured to operate the measurement circuit 30 by sending commands. The commands may include: initiate measurement, terminate measurement, read counter and reset counter. The control unit 20 may therefore be configured to determine the measurement scheme, which may comprise the initiation time and duration of one or many measurement periods for each individual detector element, used by the detector elements 15 and also to instruct the measurement circuit 30 to perform measurements according to a particular measurement scheme. The control system can, in other words be configured to apply a time-offset scheme according to an example embodiment.

The measurement data output of the CT system 10 may be extracted from the control system.

A particular embodiment of the proposed technology provides a control unit 20 wherein the at least two different detector elements 15 comprises three or more different detector elements 15 and wherein the time offset is chosen so that at least two measurement periods of the three or more different detector elements 15 at least partially overlap in time.

A possible embodiment of the proposed technology provides a control unit 20 wherein the size of the time offset is further chosen to be a fraction of the time duration of at least one of the measurement period(s).

According to another embodiment of the proposed control unit 20 there is provided a control unit 20 wherein time offset measurement scheme provides a time offset between the measurement periods for different detector elements 15 located at different depths of the same edge-on detector.

Another possible embodiment provides a control unit 20 wherein a plurality of adjacent edge-on detectors are provided with the same time offset between measurement periods.

Still another embodiment provides a control unit 20 wherein the measurement periods for the at least two different detector elements 15 located at different depths are different and wherein the time offset is a fraction of the time duration of the shorter measurement period.

According to a particular embodiment there is provided a control unit 20 wherein each of the measurement periods have the same time duration.

The proposed technology also provides a measurement circuit 30 in a Computed Tomography, CT, system 10 comprising an x-ray source and an x-ray detector array of photon counting edge-on detectors 5, wherein each edge-on detector has a number of depth-segments, also referred to as detector elements 15, arranged at different spatial locations in the direction of incoming x-rays 45. The measurement circuit 30 is configured to operate based on a time offset measurement scheme for providing a time offset between measurement periods for at least two different detector elements 15 located at different depths, wherein the time offset is chosen so that at least two measurement periods at least partially overlap in time.

Figure 11:
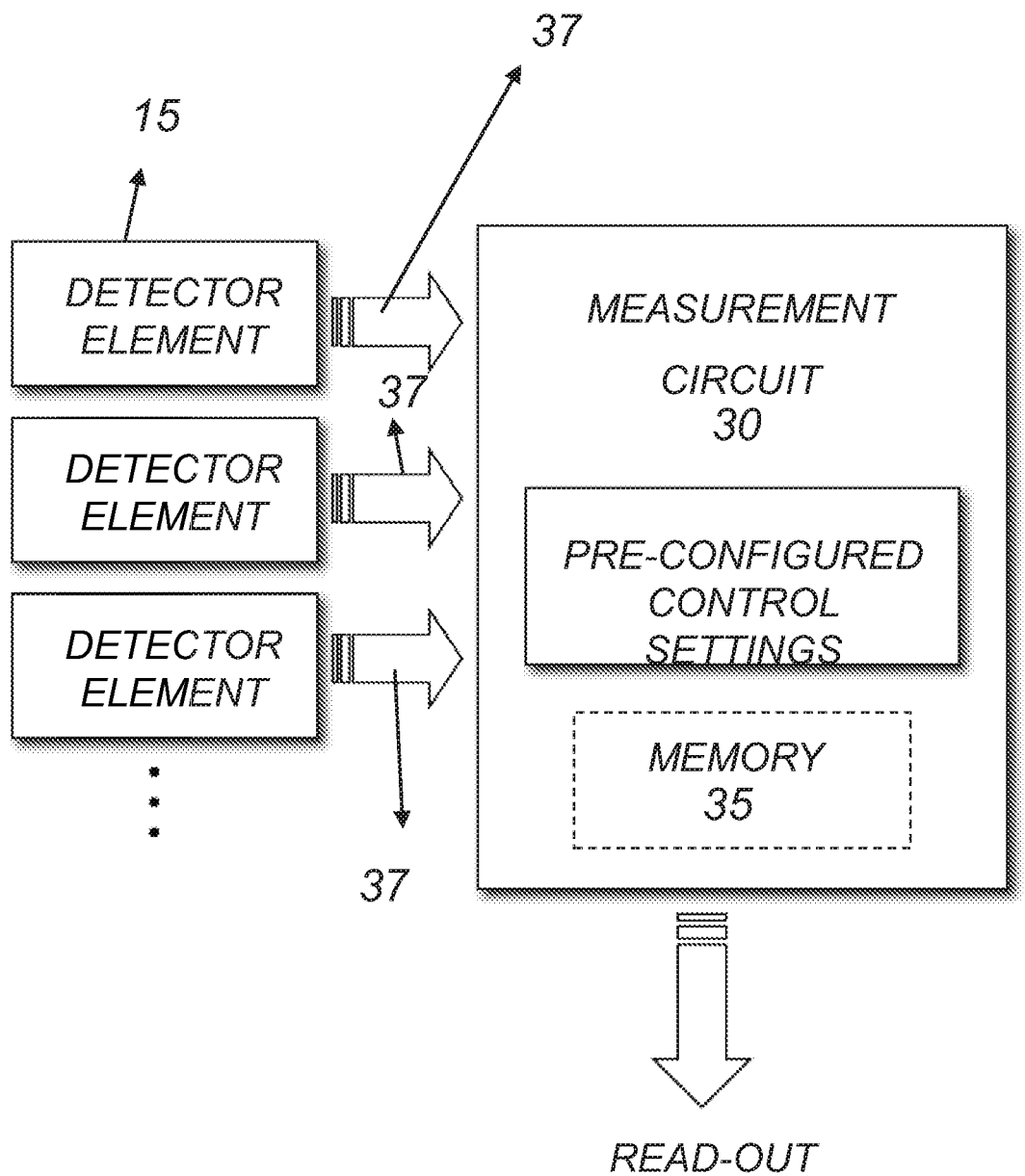
FIG. 11 is a schematic flow diagram illustrating a method for implementing pre-configured control settings in the measurement circuit of an edge-on detector.

FIG. 11 displays a schematic illustration of a measurement setup of an edge-on detector where the measurement circuit 30 comprises a set of pre-configured control settings. Each detector element on a photon-counting edge-on detector may be connected individually 37 to the measurement circuit 30. The measurement circuit 30 processes the electric charge generated from each x-ray and converts it to digital data, which can be used to obtain measurement data such as a photon count. The measurement circuit 30 may comprise one or many counters, which count the number of x-rays 45 detected by a detector element within a measurement period. The measurement circuit 30 may in particular embodiments comprise a memory 35. The measurement circuit 30 may comprise one or several processors or processing circuitries. Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs). The measurement circuit 30 comprises, in the example embodiment illustrated in FIG. 11, at set of pre-configured control settings, which may comprise the initiation time and duration of one or many measurement periods for one or many individual detector elements 15. The pre-configured control settings may, in other words, comprise a time-offset scheme for the measurement periods of the detector elements 15.

A possible embodiment of the proposed technology provides a measurement circuit 30 where the at least two different detector elements 15 comprises three or more different detector elements 15 and wherein the time offset is chosen so that at least two measurement periods of the three or more different detector elements 15 at least partially overlap in time.

Another possible embodiment provides a measurement circuit 30 wherein the size of the time offset is further chosen to be a fraction of the time duration of at least one of the measurement period(s).

By way of example, the proposed technology provides a measurement circuit 30 wherein time offset measurement scheme provides a time offset between the measurement periods for different detector elements 15 located at different depths of the same edge-on detector.

Another possible embodiment provides a measurement circuit 30 wherein a plurality of adjacent edge-on detectors are provided with the same time offset between measurement periods.

An alternative embodiment of the proposed technology provides a measurement circuit 30 wherein the measurement periods for the at least two different detector elements 15 located at different depths are different and wherein the time offset is a fraction of the time duration of the shorter measurement period.

According to a particular embodiment of the proposed technology there is provided a measurement circuit 30 wherein each of said measurement periods have the same time duration.

It will be appreciated that the methods and arrangements described herein can be implemented, combined and re-arranged in a variety of ways.

For example, embodiments may be implemented in hardware, or in software for execution by suitable processing circuitry, or a combination thereof.

The steps, functions, procedures, and/or blocks described herein may be implemented in hardware using any conventional technology, such as discrete circuit or integrated circuit technology, including both general-purpose electronic circuitry and application-specific circuitry.

Alternatively, or as a complement, at least some of the steps, functions, procedures, and/or blocks described herein may be implemented in software such as a computer program for execution by suitable processing circuitry such as one or more processors or processing units.

It should also be understood that it may be possible to re-use the general processing capabilities of any conventional device or unit in which the proposed technology is implemented. It may also be possible to re-use existing software, e.g. by reprogramming of the existing software or by adding new software components.

The invention claimed is:

1. A computed tomography (CT) system comprising:
   an x-ray source; and
   an x-ray detector array of photon-counting edge-on detectors,
   wherein each photon-counting edge-on detector has a number of detector elements, arranged at different spatial locations in the direction of incoming x-rays,
   a circuit configured to operate the computed tomography (CT) system based on a time offset measurement scheme for providing a time offset between measurement periods for at least two different detector elements located at different depths, wherein the time offset is chosen so that at least two measurement periods at least partially overlap in time.

2. The computed tomography (CT) system according to claim 1, wherein said at least two different detector elements comprise three or more different detector elements and wherein the time offset is chosen so that at least two measurement periods of said three or more different detector elements at least partially overlap in time.

3. The computed tomography (CT) system according to claim 1, wherein the size of said time offset is further chosen to be a fraction of the time duration of at least one of the measurement periods.

4. The computed tomography (CT) system according to claim 1, wherein time offset measurement scheme provides a time offset between the measurement periods for different detector elements located at different depths of each photon counting edge-on detector.

5. The computed tomography (CT) system according to claim 4, wherein a plurality of adjacent photon counting edge-on detectors are provided with a time offset between measurement periods.

6. The computed tomography (CT) system according to claim 1, wherein the measurement periods for said at least two different detector elements located at different depths are different and wherein the time offset is a fraction of a time duration of a shorter measurement period.

7. The computed tomography (CT) system according to claim 1, wherein each of said measurement periods has the same time duration.

8. A computed tomography (CT) system comprising:
   a circuit configured to control an x-ray detector array of photon-counting edge-on detectors, each detector having a number of elements, to operate based on a time offset measurement scheme for providing a time offset between measurement periods for at least two different detector elements located at different depths, wherein the time offset is chosen so that at least two measurement periods at least partially overlap in time.

9. The computed tomography (CT) system according to claim 8, wherein said at least two different detector elements comprise three or more different detector elements, and wherein the time offset is chosen so that at least two measurement periods of said three or more different detector elements at least partially overlap in time.

10. The computed tomography (CT) system according to claim 8, wherein the size of said time offset is further chosen to be a fraction of a time duration of at least one of the measurement periods.

11. The computed tomography (CT) system according to claim 8, wherein time offset measurement scheme provides a time offset between the measurement periods for different detector elements located at different depths of each photon counting edge-on detector.

12. The computed tomography (CT) system according to claim 11, wherein a plurality of adjacent photon counting edge-on detectors are provided with the same time offset between measurement periods.

13. The computed tomography (CT) system according to claim 8, wherein the measurement periods for said at least two different detector elements located at different depths are different, and wherein the time offset is a fraction of a the time duration of a shorter measurement period.

14. The computed tomography (CT) system according to claim 8, wherein each of said measurement periods has the same time duration.

15. A computed tomography (CT) system comprising:
   a circuit configured to operate based on a time offset measurement scheme for providing a time offset between measurement periods for at least two different detector elements of a photon-counting edge-on detector, the detector elements located at different depths, and wherein the time offset is chosen so that at least two measurement periods at least partially overlap in time.

16. The computed tomography (CT) system according to claim 15, wherein said at least two different detector elements comprise three or more different detector elements, and wherein the time offset is chosen so that at least two measurement periods of said three or more different detector elements at least partially overlap in time.

17. The computed tomography (CT) system according to claim 15, wherein the size of said time offset is further chosen to be a fraction of a time duration of at least one of the measurement periods.

18. The computed tomography (CT) system according to claim 15, wherein the time offset measurement scheme provides a time offset between the measurement periods for different detector elements located at different depths of each photon counting edge-on detector.

19. The computed tomography (CT) system according to claim 18, wherein a plurality of adjacent photon counting edge-on detectors are provided with the same time offset between measurement periods.

20. The computed tomography (CT) system according to claim 15, wherein the measurement periods for said at least two different detector elements located at different depths are different, and wherein the time offset is a fraction of a time duration of a shorter measurement period.

21. The computed tomography (CT) system according to claim 15, wherein each of said measurement periods has the same time duration.

22. A measurement method performed by a computed tomography (CT) system, said computed tomography (CT) system comprising an x-ray source, a circuit configured for executing the measurement method, and an x-ray detector array of photon-counting edge-on detectors, wherein each photon-counting edge-on detector has a number of detector elements, arranged at different spatial locations in the direction of incoming x-rays, wherein the measurement method comprises:

applying a time offset measurement scheme that provides a time offset between measurement periods for at least two different detector elements located at different depths, wherein the time offset is chosen so that at least two measurement periods at least partially overlap in time.

23. The measurement method according to claim 22, wherein said at least two different detector elements comprise three or more different detector elements, and wherein the measurement method further comprises choosing the time offset so that at least two measurement periods of said three or more different detector elements at least partially overlap in time.

24. The measurement method according to claim 23, wherein choosing the time offset comprises choosing the size of said time offset to be a fraction of a time duration of at least one of the measurement periods.

25. The measurement method according to claim 22, further comprising applying a time offset measurement scheme that provides a time offset between the measurement periods for different detector elements of each photon counting edge-on detector.

26. The measurement method according to claim 25, wherein applying the time offset measurement scheme comprises applying said time offset to a number of adjacent photon counting edge-on detectors.

27. The measurement method according to claim 22, wherein the measurement periods for said at least two different detector elements located at different depths are different, and wherein the time offset is a fraction of a time duration of a shorter measurement period.

28. The measurement method according to claim 22, wherein each of said measurement periods has the same time duration.

29. A non-transitory computer-readable medium having stored thereon a computer program comprising instructions, which when executed by at least one processor, cause the at least one processor to control a computed tomography (CT) system comprising an x-ray source and an x-ray detector array of photon-counting edge-on detectors, wherein each photon-counting edge-on detector has a number of detector elements, arranged at different spatial locations in the direction of incoming x-rays, wherein the at least one processor controls the computed tomography (CT) system so that the computed tomography (CT) system operates based on a time offset measurement scheme for providing a time offset between measurement periods for at least two different detector elements located at different depths, wherein the instructions comprise a requirement that the time offset is chosen so that at least two measurement periods at least partially overlaps in time.

* * * * *